United States Patent
Kramer et al.

(10) Patent No.: US 11,607,234 B2
(45) Date of Patent: Mar. 21, 2023

(54) SYSTEMS AND METHODS FOR TRAVERSING A SITE OF OBSTRUCTION

(71) Applicant: Cruzar Medsystems, Inc., Braintree, MA (US)

(72) Inventors: Thomas A. Kramer, San Carlos, CA (US); Albert K. Chin, Palo Alto, CA (US); Michael J. Glennon, Norwell, MA (US)

(73) Assignee: Cruzar Medsystems, Inc., Braintree, MA (US)

( * ) Notice: Subject to any disclaimer, the term of this patent is extended or adjusted under 35 U.S.C. 154(b) by 324 days.

(21) Appl. No.: 16/437,374

(22) Filed: Jun. 11, 2019

(65) Prior Publication Data

US 2020/0390454 A1    Dec. 17, 2020

(51) Int. Cl.
*A61B 17/22*    (2006.01)
*A61M 25/10*    (2013.01)
(Continued)

(52) U.S. Cl.
CPC .... *A61B 17/22* (2013.01); *A61B 2017/00557* (2013.01); *A61B 2017/22038* (2013.01);
(Continued)

(58) Field of Classification Search
CPC .......... A61B 17/22; A61B 2017/00557; A61B 2017/22038; A61B 2017/22051;
(Continued)

(56) References Cited

U.S. PATENT DOCUMENTS

| | | | |
|---|---|---|---|
| 3,669,099 A | 6/1972 | Silverman | |
| 3,831,587 A | 8/1974 | Boyd | |

(Continued)

FOREIGN PATENT DOCUMENTS

| | | |
|---|---|---|
| CN | 103285498 A | 9/2013 |
| EP | 0227583 A2 | 7/1987 |

(Continued)

OTHER PUBLICATIONS

International Search Report for International Application No. PCT/US2011/55149 dated Jan. 23, 2012.
(Continued)

*Primary Examiner* — Kathleen S Holwerda
(74) *Attorney, Agent, or Firm* — Greenberg Traurig, LLP; Chinh H. Pham; Joshua I. Rudawitz

(57) ABSTRACT

Systems for providing access across a site of obstruction and methods for manufacturing and using such systems are provided. Such systems may include a cannula having a lumen, an everting member coupled to the cannula, and a push assembly having a pathway. The push assembly may be slidably disposed within the lumen of the cannula and connected to a proximal end of the everting member to move the everting member from an inverted position inside the cannula to an everted position outside the cannula. The systems may also include a hard tube having a passageway, the hard tube slidably disposed on or within the pathway of the push assembly. The hard tube being designed to create and opening within and traverse and obstruction within a structure.

16 Claims, 9 Drawing Sheets

(51) Int. Cl.
    *A61M 25/01*         (2006.01)
    *A61B 17/00*         (2006.01)

(52) U.S. Cl.
    CPC ............... *A61B 2017/22051* (2013.01); *A61B 2017/22094* (2013.01); *A61M 25/0119* (2013.01); *A61M 25/10184* (2013.11)

(58) Field of Classification Search
    CPC ...... A61B 2017/22094; A61B 17/3468; A61B 17/3439; A61M 25/0119; A61M 25/10184
    See application file for complete search history.

(56) References Cited

U.S. PATENT DOCUMENTS

| | | |
|---|---|---|
| 3,911,927 A | 10/1975 | Rich et al. |
| 4,043,345 A | 8/1977 | Kramann et al. |
| 4,109,659 A | 8/1978 | Sheridan |
| 4,243,040 A | 1/1981 | Beecher |
| 4,254,774 A | 3/1981 | Boretos |
| 4,271,839 A | 6/1981 | Fogarty et al. |
| 4,360,609 A | 11/1982 | Reineke et al. |
| 4,467,816 A | 8/1984 | Schluter et al. |
| 4,493,711 A | 1/1985 | Chin et al. |
| 4,526,175 A | 7/1985 | Chin et al. |
| 4,606,347 A | 8/1986 | Fogarty et al. |
| 4,630,609 A | 12/1986 | Chin |
| 4,863,440 A | 9/1989 | Chin |
| 4,871,358 A | 10/1989 | Gold |
| 4,960,411 A | 10/1990 | Buchbinder |
| 4,990,138 A | 2/1991 | Bachich et al. |
| 5,074,845 A | 12/1991 | Miraki et al. |
| 5,171,305 A | 12/1992 | Schickling et al. |
| 5,295,960 A | 3/1994 | Aliahmad et al. |
| 5,374,247 A | 12/1994 | Lowery et al. |
| 5,389,089 A | 2/1995 | Bauer et al. |
| 5,458,573 A | 10/1995 | Summers |
| 5,630,797 A | 5/1997 | Klaus et al. |
| 6,039,721 A | 3/2000 | Kirk et al. |
| 6,042,578 A * | 3/2000 | Dinh ................... A61M 25/005 604/524 |
| 6,723,113 B1 | 4/2004 | Shkolnik |
| 6,767,338 B2 | 7/2004 | Hawk et al. |
| 6,979,290 B2 | 12/2005 | Mourlas et al. |
| 7,144,407 B1 | 12/2006 | Lasersohn |
| 7,494,485 B2 | 2/2009 | Beck et al. |
| 7,794,447 B2 | 9/2010 | Dann et al. |
| 8,343,170 B2 | 1/2013 | Massicotte et al. |
| 8,491,519 B2 | 7/2013 | Chin |
| 8,529,581 B2 | 9/2013 | Massicotte et al. |
| 8,556,851 B2 | 10/2013 | Hirszowicz et al. |
| 8,657,849 B2 | 2/2014 | Parker |
| 8,827,951 B2 | 9/2014 | Besser et al. |
| 8,894,680 B2 | 11/2014 | Hirszowicz et al. |
| 8,926,559 B2 | 1/2015 | Chin |
| 8,929,988 B2 | 1/2015 | Mitelberg et al. |
| 9,326,790 B2 * | 5/2016 | Chin ................... A61B 17/3439 |
| 9,439,662 B2 | 9/2016 | Hirszowicz et al. |
| 9,463,035 B1 | 10/2016 | Greenhalgh et al. |
| 9,782,570 B2 | 10/2017 | Hirszowicz et al. |
| 9,795,408 B2 * | 10/2017 | Chin ................... A61B 17/3468 |
| 9,814,477 B2 | 11/2017 | Jensen |
| 10,112,035 B2 | 10/2018 | Chin |
| 10,349,957 B2 * | 7/2019 | Chin ................... A61B 17/3207 |
| 10,441,755 B2 | 10/2019 | Chin et al. |
| 2002/0099396 A1 | 7/2002 | Slaker et al. |
| 2002/0120226 A1 | 8/2002 | Beck |
| 2003/0105508 A1 | 6/2003 | Johnson et al. |
| 2003/0144629 A1 | 7/2003 | Hawk et al. |
| 2005/0049718 A1 | 3/2005 | Dann et al. |
| 2006/0106361 A1 | 5/2006 | Muni et al. |
| 2007/0083158 A1 | 4/2007 | Hirszowicz et al. |
| 2009/0204069 A1 | 8/2009 | Hirszowicz et al. |
| 2010/0081965 A1 | 4/2010 | Mugan et al. |
| 2010/0249815 A1 | 9/2010 | Jantzen et al. |
| 2011/0172584 A1 | 7/2011 | Chin |
| 2011/0213469 A1 | 9/2011 | Chin et al. |
| 2012/0149983 A1 | 6/2012 | Chin |
| 2012/0150110 A1 | 6/2012 | Chin |
| 2012/0302996 A1 | 11/2012 | Barash et al. |
| 2014/0066961 A1 | 3/2014 | Chin et al. |
| 2014/0343593 A1 | 11/2014 | Chin et al. |
| 2015/0066068 A1 | 3/2015 | Hirszowicz et al. |
| 2015/0088187 A1 | 3/2015 | Chin |
| 2015/0126966 A1 | 5/2015 | Hirszowicz et al. |
| 2015/0142045 A1 * | 5/2015 | Bacich ................... A61F 2/0027 606/193 |
| 2016/0278747 A1 | 9/2016 | Chin et al. |
| 2017/0360475 A1 | 12/2017 | Chin et al. |
| 2018/0035983 A1 | 2/2018 | Lonky |
| 2018/0125510 A1 * | 5/2018 | Chin ................... A61B 17/3207 |
| 2018/0333545 A1 | 11/2018 | Yurek et al. |
| 2019/0000429 A1 | 1/2019 | Magana et al. |
| 2019/0009058 A1 | 1/2019 | Bachich et al. |
| 2020/0205795 A1 | 7/2020 | Chin et al. |
| 2020/0330082 A1 | 10/2020 | Chin et al. |

FOREIGN PATENT DOCUMENTS

| | | |
|---|---|---|
| EP | 0359489 A2 | 3/1990 |
| EP | 0227583 B1 | 8/1992 |
| EP | 0746227 B1 | 7/2004 |
| EP | 1494524 A2 | 1/2005 |
| EP | 2979722 A3 | 4/2016 |
| GB | 1482873 A | 8/1977 |
| JP | S50-149171 A | 11/1975 |
| JP | S58-500694 A | 5/1983 |
| JP | S59-501149 A | 7/1984 |
| JP | S62170260 A | 7/1987 |
| JP | 2001238957 A | 9/2001 |
| JP | 2008161239 A | 7/2008 |
| JP | 6506130 B2 | 4/2019 |
| WO | 1982003989 A1 | 11/1982 |
| WO | 84/00113 A1 | 1/1984 |
| WO | 2000007657 A1 | 2/2000 |
| WO | 2001/83017 A1 | 11/2001 |
| WO | 2003/084584 A2 | 10/2003 |
| WO | 2003084584 A3 | 2/2004 |
| WO | 2011088381 A1 | 7/2011 |
| WO | 2012048142 A1 | 4/2012 |
| WO | 2017/205001 A1 | 11/2017 |

OTHER PUBLICATIONS

International Search Report in International Application No. PCT/US2017/059972 dated Feb. 28, 2018.

International Search Report in International Application No. PCT/US2020/037139 dated Aug. 27, 2020.

\* cited by examiner

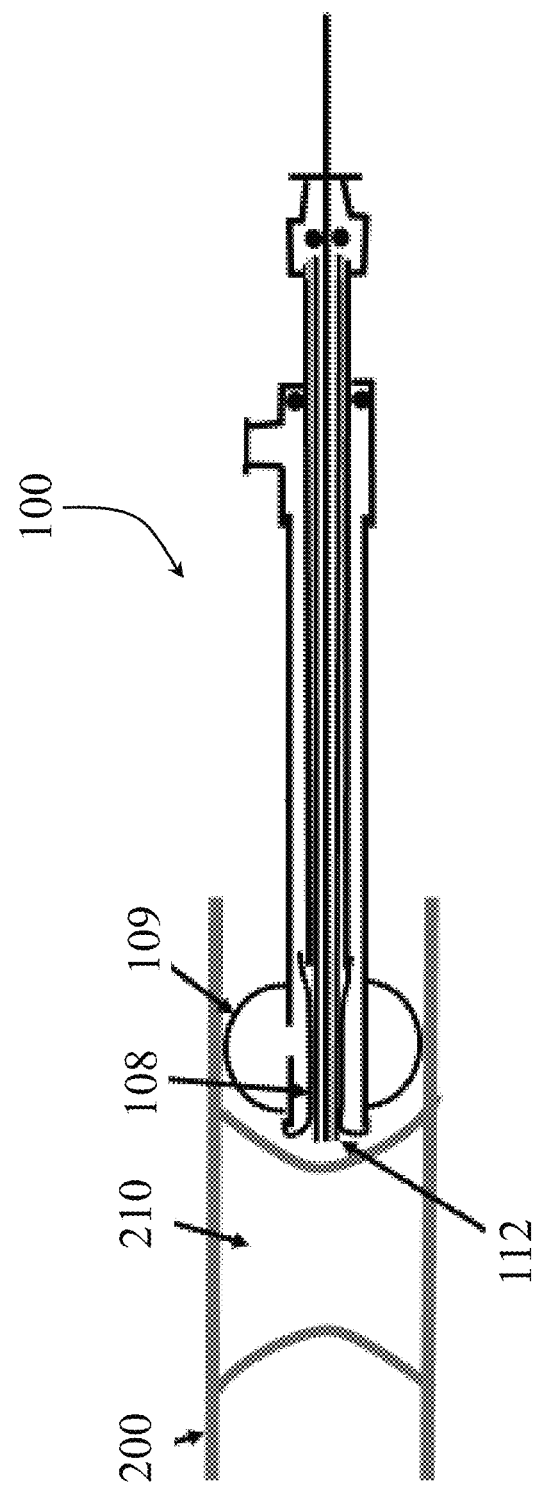

SYSTEMS AND METHODS FOR TRAVERSING A SITE OF OBSTRUCTION

FIELD OF THE INVENTION

The present invention relates to systems and methods suitable for traversing a site of obstruction within a structure such as vessel or tube. In particular, the present invention relates to an everting sleeve catheter that drives a hard tube through an obstruction in a vessel or other luminal structure, while preserving internal guidewire mobility.

BACKGROUND

Obstructions within pipes, tubes, body cavities, and vessels can often inhibit access through the pipes, tubes, body cavities, and vessels. For example, disuse, low flow, slow flow, contaminants, unwanted chemical reactions, and/or obstructive material that can narrow or block pipes, tubes, or drains in a household, commercial, laboratory, or industrial setting. Similarly, for example, atherosclerosis and other circulatory diseases occur when the arteries become narrowed or blocked. Plaque formation within the arteries can cause occlusive lesions or other obstructions on the artery wall. Similarly, clots, thrombus, stenosis, or tortuosity in a vessel can also act to inhibit access or movement through the vessel. Such an obstruction can also cause health problems by impeding movement of fluid through the vessel. For example, if the vessel is a blood vessel, the obstruction may impede blood flow.

Some conventional systems include using a guidewire that is directed through the lumen of the everting member. The system can be configured such that the guidewire is pushed into the site of obstruction. However, in situations where the obstruction is dense and the guidewire is flexible, the flexibility of the distal tip of guidewire can cause it to bend over and deform, rather than pierce into obstruction, resulting in the guidewire failing to traverse the site of obstruction. For example, physicians may reluctant to advance a stiff wire through a vessel, as it has a greater potential of perforating the vessel upon passage, particularly upon encountering a stenosis or obstruction. A spring guidewire can contain a curved, floppy tip that may be advanced with less incidence of perforation. However, upon contact with an obstruction that may be either fibrous or calcific, the guidewire may have limited crossing ability, as it readily bends and deforms upon contact with the obstruction.

Clinical use of the previous systems in atherosclerotic arterial obstructions demonstrate that the previous systems have limitations in traversing the site of an obstruction. Arterial obstructions may be composed of fibrous tissue incorporating calcified material, making the obstruction rock hard and difficult to penetrate. For example, if penetration of an obstruction is attempted by driving a guidewire into the lesion with an everting member, the limited column strength of a guidewire causes it to collapse, rather than to cross the obstruction. A standard guidewire contains an outer spring winding, and often a floppy distal tip. The floppy tip bends over upon advancement through the vasculature, to decrease the potential of guidewire perforation of the vessel, compared to advancement of a straight, stiff wire.

Accordingly, it would be desirable to have a system that can provide access across an obstruction in a pipe, tube, body cavity, or vessel in order to provide easier passage therethrough while minimizing potential damage to the walls of the pipe, tube, body cavity, or vessel.

SUMMARY

There is a need for improvements for traversing an obstruction or occlusion within a structure. The present invention provides, in various embodiments solutions to address this need, in addition to having other desirable characteristics.

In accordance with example embodiments of the present invention, a device for providing access across a site of obstruction is provided. The device includes a cannula having a proximal end, a distal end, and a lumen extending therebetween, a hard tube being slidably movable longitudinally within the lumen, and an everting member, having a first end coupled to the distal end of the cannula and a second end. Advancement of the hard tube within the lumen moves the everting member from an inverted position within the lumen to an everted position outside the cannula.

In accordance with aspects of the present invention, the device also includes an anchoring member circumferentially placed about an outer surface of the cannula and in the fluid communication with the lumen. The lumen can provide a path along which pressurizing fluid can be introduced and evacuated from the cannula, such that in the presence of pressurizing fluid, the anchoring member inflates while the everting member compresses onto the hard tube, and in the absence of pressurizing fluid, the anchoring member deflates while the everting member decompresses from the hard tube. The anchoring member can be in the fluid communication with the lumen of the cannula and being expandable from a depressurized position to a pressurized position anchors the cannula near a site of obstruction when the lumen is pressurized to an anchoring pressure sufficient to anchor the cannula in proximity to the site of obstruction. The device can further include a bushing disposed at the distal end of the cannula to couple the first end of the everting member to the distal end of the cannula. The device can further include a sealing member disposed between walls of the lumen and the push assembly to seal the lumen. The device can further include a sealing member disposed between walls of the pathway and the tube to seal the pathway. At least one of the push assembly and the hard tube can be configured to receive a guidewire therethrough.

In accordance with example embodiments of the present invention, a system for providing access across a site of obstruction is provided. The system includes a cannula having a proximal end, a distal end, and a lumen extending therebetween, an everting member, having a first end coupled to the distal end of the cannula and a second end, a push assembly, positioned within the lumen, having a pathway along its entire length, the push assembly being slidably disposed across the proximal end of the cannula into the lumen of the cannula and being connected at its distal end to the second end of the everting member, such that advancement of the push assembly along the lumen of the cannula moves the everting member from an inverted position within the lumen of the cannula to an everted position outside the cannula, and a hard tube being fixedly attached to the push assembly, the hard tube being slidably movable across a proximal end of the push assembly.

In accordance with aspects of the present invention, the system also includes an anchoring member circumferentially placed about an outer surface of the cannula and in the fluid communication with the lumen. The lumen can provide a path along which pressurizing fluid can be introduced and evacuated from the cannula, such that in the presence of pressurizing fluid, the anchoring member inflates while the everting member compresses onto the hard tube, and in the absence of pressurizing fluid, the anchoring member deflates while the everting member decompresses from the hard tube. The anchoring member can be in the fluid communication with the lumen of the cannula and being expandable from a depressurized position to a pressurized position anchors the cannula near a site of obstruction when the lumen is pressurized to an anchoring pressure sufficient to anchor the cannula in proximity to the site of obstruction. The system can further include a guidewire configured for passage through at least one of the push assembly and the hard tube. The system can further include an injection port configured to couple to a pressurization source configured to inject fluid to pressurize the lumen and extract the fluid to depressurize the lumen.

In accordance with example embodiments of the present invention, a method for traversing a site of obstruction is provided. The method includes providing an everting member in a depressurized and an inverted state within a lumen of a cannula, pressurizing the everting member to grip the hard tube, advancing a hard tube longitudinally within the lumen of the cannula, and everting the everting member from the cannula to distally advance the hard tube gripped by the everting member outside the cannula and into the obstruction. The method also includes depressurizing the everting member to release the hard tube, retracting the hard tube longitudinally into the lumen of the cannula, and inverting the everting member into the lumen.

In accordance with aspects of the present invention, the pressurizing the everting member to grip the hard tube comprises pressurizing the lumen of the cannula to compress the everting member onto the hard tube. The pressurizing the lumen of the cannula can further include pressurizing an anchoring member coupled to the cannula to expand and contact an inner wall of a vessel to anchor the cannula near the site of obstruction within the vessel. The method can further include re-pressurizing the everting member to grip the hard tube and re-everting the everting member from the cannula to further distally advance the hard tube gripped by the everting member. The step of everting the everting member can further include advancing a push assembly connected to a proximal end of the everting member to move the everting member from an inverted position inside the cannula to an everted position outside the cannula. The method can further include advancing a guidewire through an opening created by the hard tube contacting the obstruction.

BRIEF DESCRIPTION OF THE FIGURES

These and other characteristics of the present invention will be more fully understood by reference to the following detailed description in conjunction with the attached drawings, in which:

FIGS. 3A, 3B, and 3C show cross-sectional views of a device for traversing an obstructing in accordance with an embodiment of the present invention.

DETAILED DESCRIPTION

Figure 1A:
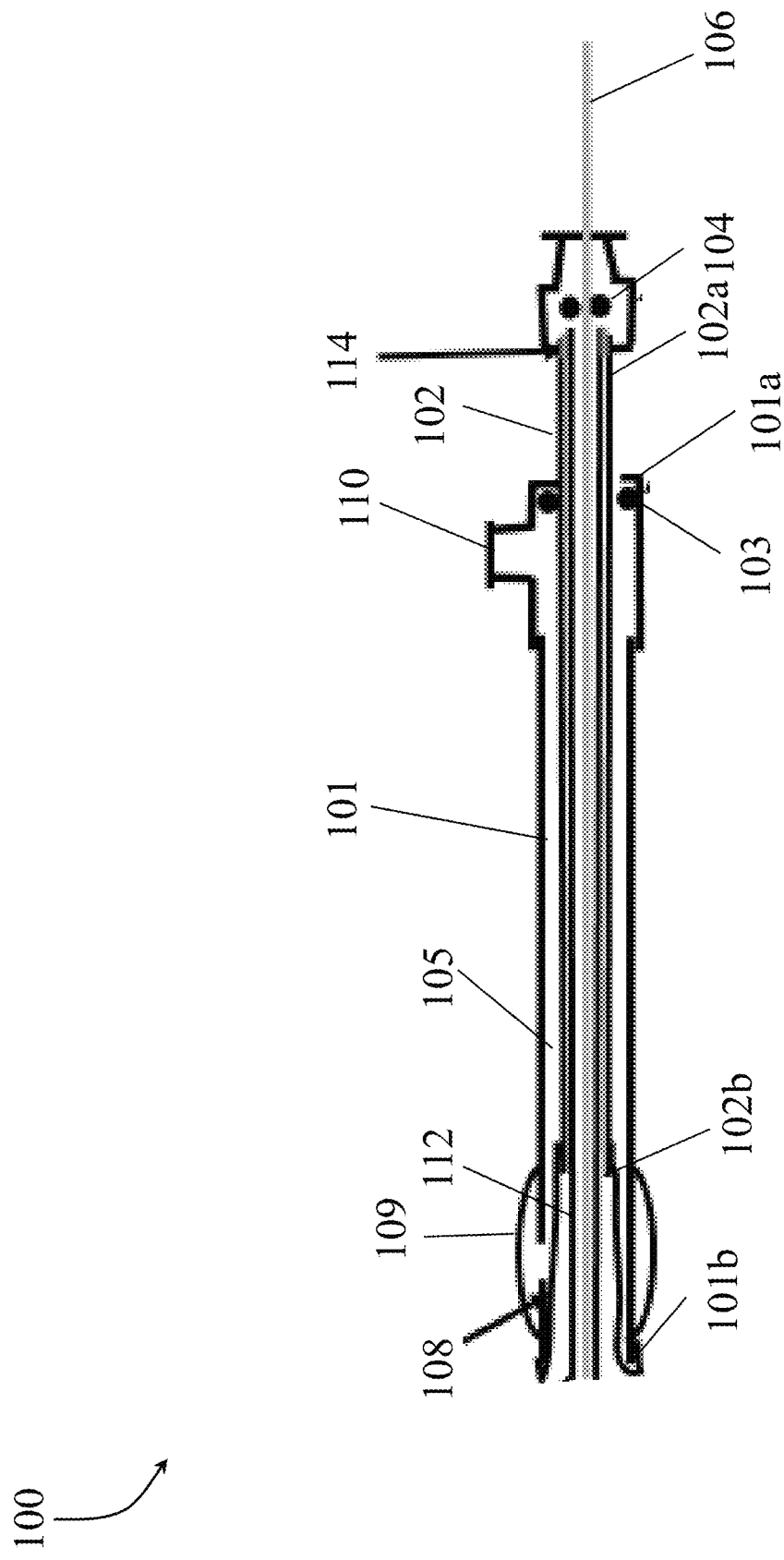
FIGS. 1A, 1B, and 1C show cross-sectional views of a device for traversing an obstruction in accordance with an embodiment of the present invention.

An illustrative embodiment of the present invention relates to systems and methods for providing access across a site of obstruction. In embodiment, the system includes a cannula, a push assembly having a pathway and slidably situated within the cannula, an everting member, for example, approximately 2-4 cm long attached at one end to the cannula and at the other end to the push assembly, and a substantially rigid tube attached to the push assembly. The rigid tube, in embodiment, can run the length of the cannula and can protrude from the distal tip of the cannula. In an embodiment, the protrusion of the rigid tube from the push assembly can be a distance of about 2-3 mm. Upon pressurization of the cannula to evert the everting member and advancement of the push assembly, the rigid tube can be driven into the site of obstruction. The advancement of the rigid tube, in one embodiment, may be limited to about 1-2 cm, to minimize any opportunity for vessel perforation. Once the rigid tube is advanced into the obstruction, the everting member can be inverted along with the rigid tube into the cannula, and the cannula advanced forward into the space created by the advancement of the rigid tube. The process of re-pressurized the cannula eversion of the everting member and the advancement of the rigid tube into the obstruction can be repeated, with subsequent inversion of the everting member and withdrawal of the rigid tube into the cannula until the obstruction has been traversed.

FIGS. 1A through 3C, wherein like parts are designated by like reference numerals throughout, illustrate an example embodiment or embodiments of improved operation for systems and methods for traversing a site of an obstruction, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

In accordance with some embodiments of the present invention, systems and methods are provided for providing access across an obstruction, such as an obstruction observed in connection with a complete or partial blockage within a vessel caused by, for instance, a clot, stenosis, calcification, or tortuosity within a blood vessel. The systems and methods described below may also, in some instances, be used to navigate past difficult regions in vessels, including arteries, veins, ureters, urethra, Fallopian tubes, pancreatic ducts, nasal sinuses, or any luminal structures or cavities in the body as well as pipes, ducts, tubes, or other passages in an industrial, commercial, household, or laboratory setting.

Figure 1B:
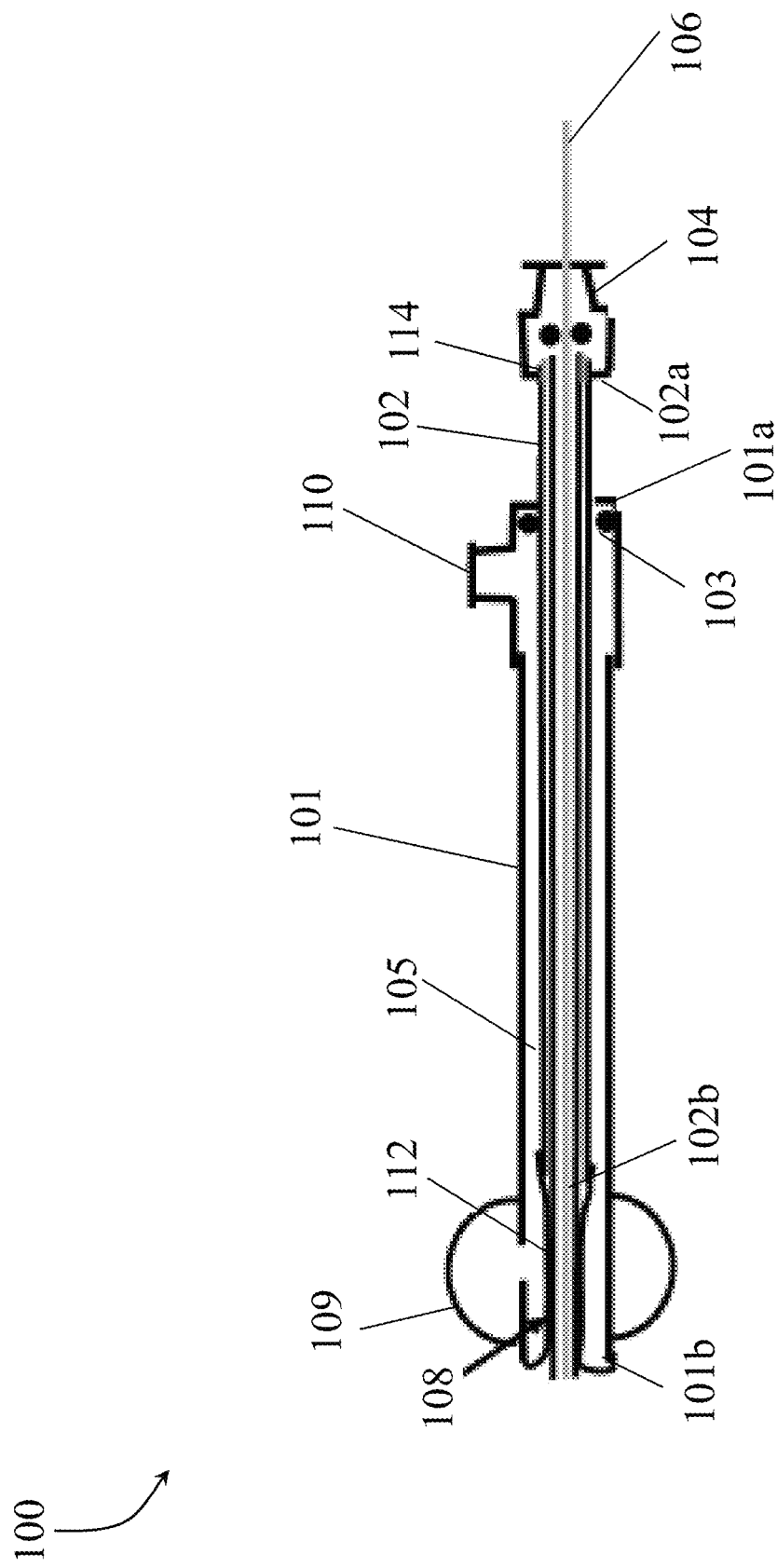
Figure 1C:
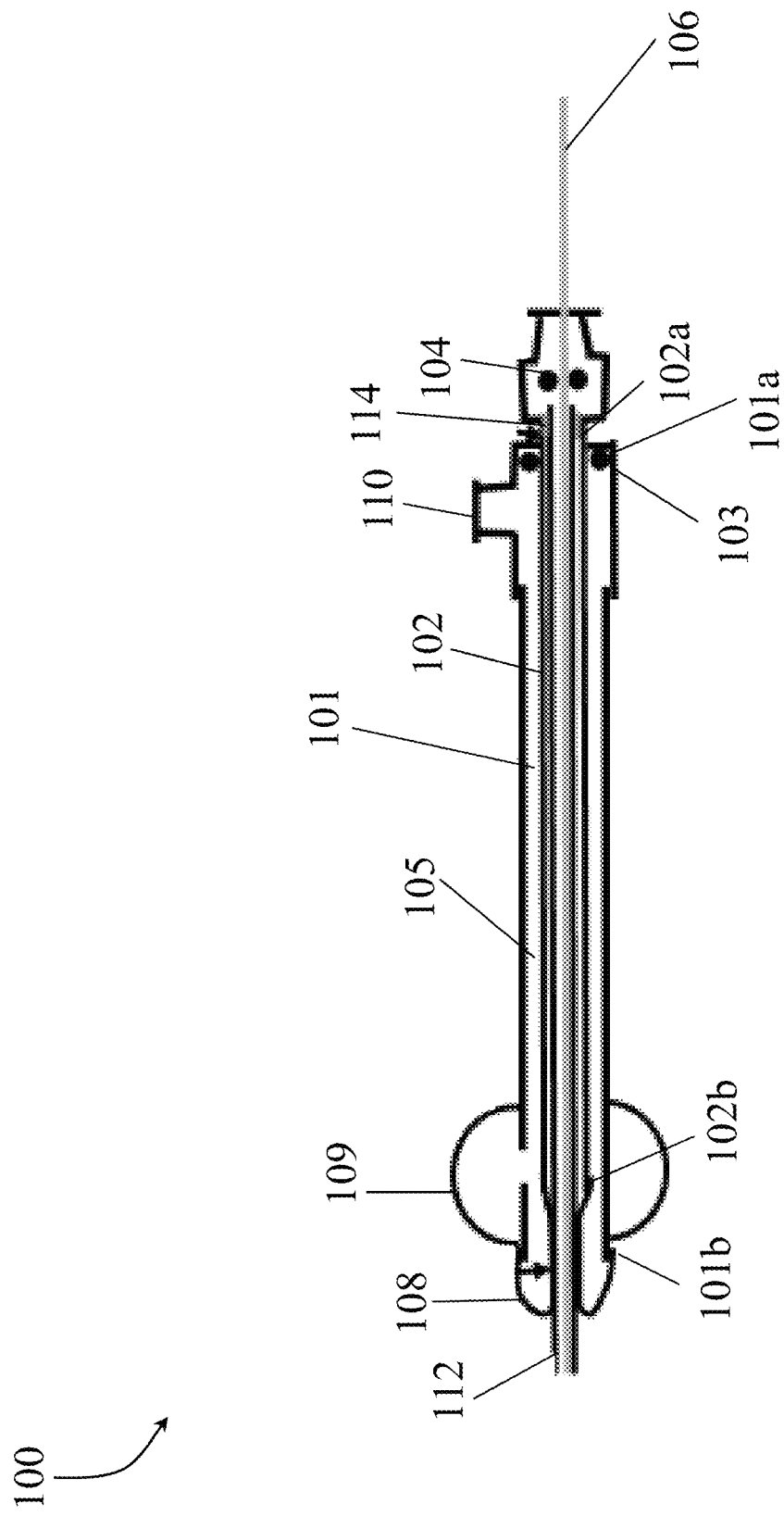

Referring now to FIGS. 1A-1C, a cross-sectional view of an exemplary device 100 for providing access across a site of an obstruction is provided. The device 100, in some embodiments, includes a cannula 101 defining an open-ended channel or lumen 105 extending between a proximal end 101a and a distal end 101b thereof. The cannula 101 can be sized, dimensioned, and scaled for insertion into the obstructed pathway, such as a vessel, artery, tube, pipe, pipeline, or other passageway and navigation to the site of obstruction. As illustrated in FIG. 1A, the cannula 101 can be substantially tubular, cylindrical, circular, etc. in shape. It should be noted, however, that while described as being tubular in shape, the cannula 101 may have any other shape desired depending on the particular application, as the shape of the cannula 101 may aid in the navigation of the cannula 101 to provide access across a site of obstruction. For example, the cannula 101 can include any combination of polygonal shapes known in the art without departing from the scope of the present invention.

In some embodiments, the cannula 101 may be sufficiently flexible so that it can navigate through a tortuous passageway in a vessel, tube, or pipe. Additionally or alternatively, the cannula 101 may be sufficiently axially rigid so that it does not bend or fold in the presence of a proximal force being applied for advancing cannula 101 through the vessel, tube, or pipe. The cannula 101 may also have any desired length, depending upon the application, so long as cannula 101 can be advanced through a passageway (e.g., a vessel) to the site of obstruction. For example, in some embodiments, cannula 101 may be relatively long, such as for example, a long catheter, so that it can be advanced through a long or tortuous passageway to a site of obstruction. In another embodiment, cannula 101 may be relatively short in length to be delivered across the obstruction. The cannula 101 may also have any diameter sufficient to allow the cannula 101 to fit within a passageway, depending upon the application and the size of the passageway. In an embodiment, the diameter of the cannula 101 may remain substantially constant throughout. If desired, the diameter of the cannula 101 may vary, as necessary, along the length of the cannula 101. For example, the distal end 101a may be smaller in diameter than the proximal end 101b or vice versa.

In some embodiments, the cannula 101 may include a coating on an outer surface to reduce friction between the cannula 101 and any sidewalls upon insertion into a passageway. In some embodiments, the coating may cover the entire outer surface of the cannula 101. In an alternative embodiment, the coating may be located only at a distal end 101b of the cannula 101. However, it will be apparent in view of this disclosure that the coating may be placed onto the outer surface in other manners as well. Similarly, the cannula 101 may include a coating on an inner surface to reduce friction of components moving within the inner channel of the cannula 101. In some embodiments, the inner coating may cover the entire inner surface of the cannula 101. In some embodiments, the coating may be located only at the distal end 101b of the cannula 101. It will be apparent in view of this disclosure that the coating may be placed onto the inner surface in other manners as well.

In some embodiments, a push assembly 102 can be placed across the proximal end 101a and into the cannula 101. The push assembly 102 can include a proximal end 102a and a distal end 102b. The push assembly 102, depending on the design and the application, can be a catheter, tube, pipe, or any other structure having a pathway extending therethrough. The push assembly 102, in some embodiments, may be constructed of a sufficiently rigid material such as metal, stainless steel, or a reinforced plastic catheter section to provide advancement/retraction within the lumen 105 of the cannula 101 in accordance with the various embodiments of the present invention. The push assembly 102 may be constructed as a single integral piece or, in some embodiments, can be constructed from multiple pieces. At least a portion of the proximal end 102a of the push assembly 102, in some embodiments, can be slidably disposed within lumen 105 of the cannula 101 to allow a user to manually (or by a mechanical application of force) advance or retract within the push assembly 102 within lumen 105 of the cannula 101. Thus, movement of the push assembly 102 is permitted in a longitudinal direction within the cannula 101.

In some embodiments, the push assembly 102 can include one or more coatings such as, for example, hydrophilic coatings, anti-thrombogenic coatings, hydrophobic coatings, silicone coatings, or tetrafluoroethylene (TFE) coatings. The coatings can be on an outside surface of the push assembly 102 for assisting in passage within the cannula 101 and/or the vessel 200. Similarly, the coatings can be on an internal surface of the push assembly 102 to assist in the passage of other devices within the push assembly 102 (e.g., guidewire 106).

In some embodiments, to provide a substantially fluid tight seal between the proximal end 101a of cannula 101 and the push assembly 102 extending therethrough, seal 103 can be provided at a proximal end 101a of the cannula 101. The fluid tight seal 103 can include any combination of mechanisms configured to form a fluid or air tight seal between the inner channel of the cannula and the outer sidewalls of the push assembly 102. For example, the seal 103 can be a sliding O-ring seal (also known as a Tuohy-Borst seal) may be provided on a fitting at the proximal end of cannula 101. that does not collapse within the sliding seal 103. In some embodiments, the seal 103 in the proximal end 101a of cannula 101 can act to limit the length which the push assembly 102 can be retracted from the cannula. For example, as the push assembly 102 is retracted through the fluid tight seal 103, the push assembly 102 can include a stop member (not shown) for contacting the fluid tight seal 103, thus limiting an amount that the push assembly 102 can be retracted. Similarly, the fluid tight seal 103 can act to limit the distance along which the push assembly 102 can be extended into and/or out of the distal end 101b of the cannula 101. It should of course be noted that other methods may be used to limit the extent of extension and retraction of the push assembly 102. In some embodiments, a short, outer rigid stainless-steel sleeve may be used to reinforce the proximal end of the push assembly 102 as it inserts into an inflation port 110 on the proximal end of the cannula 101.

In some embodiments, the proximal end 102a of push assembly 102 can include a sliding seal 104 that is designed to seal against a sliding tube (not shown) and/or a guidewire 106. The sliding seal 104 can be similar in structure as the fluid tight seal 103 or it can be a different construction. For example, the sliding seal 104 can be a Tuohy-Borst seal. The sliding seal 104 can be designed to enable instruments or other tubes or catheters to be passed through the proximal end 102a of the push assembly 102 and provide into and/or through the channel of the cannula 101, for example, during traversal of the site of obstruction. In some embodiments, the sliding seal 104 can have a passageway that extend therethrough and can enable passage of other objects, guidewires, additional tubes, microcatheters, fluids, gases, etc. For example, the sliding seal 104 can include a fluid seal that can slide along the guidewire 106 when the guidewire 106 is extending through the passageway and can maintain a fluid seal (e.g., a hemostatic seal) between the sliding seal 104 and an object extending therethrough (e.g., guidewire 106).

In some embodiments, a guidewire 106 can be introduced through the passageway of the cannula 101 for guiding placement of the device 100. The guidewire 106, in some embodiments, can be any suitable guidewire 106 for extending through the passageway of the push assembler 102 or hard tube 112. In some embodiments, the guidewire 106 can be constructed, for example, from one or more of gold, Nitinol, platinum, stainless steel, nickel, titanium, tungsten, alloys thereof, or combinations thereof. In some embodiments, the guidewire 106 can include one or more coatings such as, for example, hydrophilic coatings, anti-thrombogenic coatings, hydrophobic coatings, silicone coatings, or tetrafluoroethylene (TFE) coatings. More generally, the guidewire 106 can be any suitable material or construction. In some embodiments, the guidewire 106 can be configured to pass through the length of cannula 101, and lie flush with or fall short of the distal end 101*b* of the cannula 101.

In some embodiments, an everting member 108 can be located at a distal end 101*b* of the cannula 101. In some embodiments, one end of the everting member 108 can be coupled to the distal end 101*b* of the cannula 101 and an opposing end of the everting member 108 can be coupled to a distal end 101*b* of the push assembly 102. The everting member 108 can be coupled to any combination of the tip, the inner side, or the outer side of the cannula 101 and the push assembly 102. For example, as depicted in FIG. 1A, the everting member 108 is coupled to the outer side of the cannula 101 and the outer side of the push assembly 102.

The everting member 108, in some embodiments, can be a thin-walled polymer sleeve, approximately 0.0002"- 0.0004" thick, constructed of PET (polyethylene terephthalate), Nylon 12 or similar inelastic material. In some embodiments, the sleeve can be 0.0003" thick. In some embodiments, the everting member 108 and push assembly 102 may be constructed of similar polymeric material, such as for example, Nylon 12, allowing them to be joined together using heat bonding. As would be appreciated by one skilled in the art, the everting member 108 may be of any thickness and may be attached to the push assembly 102 using any combination of methods known in the art, for example, a mechanical coupling, an adhesive bond, or a combination thereof. In some embodiments, the everting member 108 can include any flexible or deformable, substantially fluid impermeable material capable of being pressurized and/or depressurized by introduction of a fluid, for example, within the lumen 105 or internal channel of the cannula 101. For example, in some embodiments, the everting member 108 can be made of one or more of PET, nylon, nylon elastomers, polyurethane, other suitable flexible or deformable materials, or combinations thereof.

In some embodiments, when the lumen 105 of the cannula 101 is pressurized, the everting member 108 can be designed to collapse, compress, and/or evert from the inside of the cannula 101. In some embodiments, the everting member 108 can also evert and/or collapse, via pressurization within the lumen 105 of the cannula 101 (e.g., via injection of a fluid). Similarly, in some embodiments, when a negative pressure is applied (e.g., via application of a vacuum or extraction of a fluid) to the lumen 105 of the cannula 101, the everting member 108 can be designed to contract and/or invert back inside of the cannula 101. In some embodiments, the everting member 108, although flexible, can be substantially inelastic to withstand relatively high pressurization levels and to provide more precise control over eversion and inversion distances.

In some embodiments, the push assembly 102 can be used in combination with the pressurization/depressurization of the cannula 101 lumen 105 can be designed to advance or retract (evert or invert) the everting member 108. The push assembly 102 can be sufficiently rigid to enable longitudinal displacement of the push assembly 102 as the user or a drive mechanism pushes on the proximal end 102*a* and to deliver an eversion or inversion force to the everting member 108.

In some embodiments, the push assembly 102 may be configured to limit the extent of eversion and re-inversion of the everting member 108 to control the extent of eversion. The push assembly 102 may be longer than, shorter than, or equal in length to the everting member 108. The proximal end 102*a* of the push assembly 102 can, in some embodiments, protrude proximally out of the cannula 101. By way of a non-limiting example, in connection with embodiments, eversion may be limited. For example, as everting member 108 fully everts, the distal end 102*b* of the push assembly 102 can travel in distal direction until it reaches the bushing, which will act as an eversion stop to prevent push assembly 102 from exiting cannula 101.

In some embodiments, the push assembly 102 can be designed such that by pulling back on the proximal end 102*a* with a partially pressurized or depressurized everting member 108 can cause the everting member 108 to re-invert. The re-inversion may be limited to prevent tear or detachment of the everting member 108 from the cannula 101 due to undue traction exerted on the everting member 108.

As described with greater detail below, the everting member 108, in some embodiments, can be configured to compress onto, collapse onto, grip, and/or grasp (i.e., by friction) and advance at least one of the sliding tube (not shown) and the guidewire 106 in response to advancement of the push assembly 102. In some embodiments, such configurations permit the user to exercise more precise control over deployment of the everting member 108 and guidewire 106.

In some embodiments, the device 100 can include an anchor 109 designed to anchor the device 100 at a desired location (e.g., site of an obstruction). The anchoring portion 109 can include any flexible or deformable, substantially fluid impermeable material capable of being pressurized and/or depressurized by introduction of a fluid. For example, in some embodiments, the anchoring member can be a balloon or similar object made of one or more of latex, rubber, PET, nylon, nylon elastomers, polyurethane, other suitable flexible materials, or combinations thereof. In some embodiments, the anchoring portion 109 and cannula 101 may be constructed of similar polymeric material, such as for example, Nylon 12, allowing them to be joined together using heat bonding. As would be appreciated by one skilled in the art, the anchoring portion 109 may be attached to the cannula 101 using any combination of methods known in the art, for example, a mechanical coupling, an adhesive bond, or a combination thereof.

In some embodiments, the anchoring portion 109 can be flexible and either elastic or inelastic so long as the anchoring member can withstand pressurization without bursting. In general, the anchoring portion 109 can be any pressurizable member capable of fixing the system 100 in place within the pipe, tube, vessel, passage, etc. during traversal of the site of obstruction. anchoring portion 109

In some embodiments, the anchor 109 can reside on the outside near the distal end of cannula 101. The anchor 109 can be located at any position on the cannula 101 that may apply sufficient anchoring force to hold the device 100 in place during operation. In some embodiments, the cannula 101 can include an opening to the interior of the anchoring portion 109 to enable pressurization and depressurization from the lumen 105 of the cannula 101 to cause the anchor 109 to inflate. In some embodiments, the anchor 109 is in fluid communication with a same channel or lumen 105 as the everting member 108, such that the anchor 109 and everting member 108 are pressurized and depressurized substantially simultaneously. For example, during pressurization, the everting member 108 can compress and/or evert from within the cannula 101 while the anchor 109 inflates, as shown in FIG. 1B.

In some embodiments, the cannula 101 can include injection port 110 in fluid communication with the lumen 105 of the cannula 101 and the everting member 108 and the anchor 109. The cannula 101 can be designed for pressurizing and depressurizing the lumen 105 of the cannula 101 through the injection or evacuation of pressurized fluid or gas. For example, in some embodiments, fluids such as, for example, air, saline solution, water, any other suitable fluid, or combinations thereof can be introduced or evacuated from the lumen 105 of the cannula 101 via the port 110. The port 110, in some embodiments, may be a tube, pipe, or other passage, for example, through which fluid can flow. In some embodiments, port 110 may be permanently or detachably coupled to the cannula 101. In some embodiments, port 110 may be integral with the cannula 101. To that end, the cannula 101 and the port 110 may be manufactured as a single unit.

In some embodiments, the port 110 can be utilized to pressurize or depressurize any components in fluid communication with the lumen 105 of the cannula 101. For example, upon injection or evacuation of pressurized fluid from the lumen 105 of the cannula 101 via injection port 110, pressurization and depressurization of the everting member 108 and/or the anchor 109 can be achieved. In some embodiments, the everting member 108 or the anchoring portion 109 can include a separate valve or other resealable mechanism to permit independent pressurization and depressurization of the everting member 108 and the anchoring portion 109. For example, a second port (not shown) can be included on the cannula 101 to provide independent pressurization and depressurization of the anchoring portion 109.

In some embodiments, the port 110 can include a connector integrated with the port 110 to facilitate coupling of the port 110 to an inflation mechanism (not shown), that can direct fluid into and out of the lumen 105 through port 110. The inflation mechanism may be a pump (e.g. a manual or automatic pump), syringe, or other device that can pressurize and/or depressurize (e.g., inflate or deflate) the everting member 108 during use. In some embodiments, the port 110 may be utilized as a pressurization port to collapse on/compress onto the everting member 108 and/or the anchor 109 by fluidly connecting the everting member 108 and/or the anchor 109 to the inflation mechanism. It will be apparent in view of this disclosure that, in some embodiments, other locations and configurations for the inflation port are possible as long as fluids can enter with a sufficient force to pressurize and depressurize the everting member 108 and/or the anchor 109. In some embodiments, the port 110 may be sealable to provide a fluid seal between the lumen 105 of the cannula 101 and the ambient space.

In operation, the combination of components of the device 100 can be utilized to traversing a site of obstruction. Referring to FIG. 1A, a depressurized state of the device 100 is depicted. In the depressurized state, the anchor 109 is deflated and the everting member 108 is not pressurized and inverted within the cannula 101. When in the depressurized state, the device 100 can be navigated to a site of an obstruction. Referring to FIG. 1B, a pressurized state of the device 100 is depicted. In the pressurized state, the anchor 109 is inflated and the everting member 108 is pressurized within the cannula 101 to compress onto the push assembly 102 or guidewire 106. The object being compressed by the everting member 108 will depend on the longitudinal location of the respective push assembly 102 and the guidewire 106 within the cannula 101. For example, as depicted in FIG. 1B, the everting member 108 compressed on the guidewire 106. When in the depressurized state, the device 100 can be navigated to a site of an obstruction.

Referring to FIG. 1C, once the everting member 108 compresses on an object, the target object and the everting member 108 can be everted from the interior of the cannula 101. In some embodiments, to evert the target object and the everting member 108, the push assembly 102 can be advanced forward inside lumen 105 of cannula 101, causing the everting member 108 to evert distally, driving compressed target object forward. For example, as depicted in FIG. 1C, the longitudinal advancement of the push assembly 102 toward the distal end 101b of the cannula 101 can cause the everted member 108 to compressed onto the guidewire 106 (e.g., from FIG. 1B) to be advanced outside of the cannula 101.

In some embodiments, the everting member 108 can be depressurized while outside of the cannula 101. In the everted and depressurized state (e.g., through an application of a vacuum), the anchor 109 is deflated and the everting member 108 is uncompressed (e.g., from the push assembly 102) outside of the cannula 101. Additionally, when in the everted and depressurized state, any combination of the push assembly 102 and the guidewire 106 can be advanced or retracted longitudinally from within the cannula 101.

In some embodiments, the device 100 can include a hard tube 112 that is fixedly attached to the push assembly 102. The hard tube 112 can be fixedly attached to an interior or exterior portion of the push assembly 102 and can move longitudinally within the cannula 101 with the push assembly 102. In some embodiments, the hard tube 112 can be fixedly attached to the push assembly 102 using an adhesive bond 114 at the proximal end of push assembly 102. The hard tube 112 can be fixedly or removably attached to the push assembly 102 using any combination of systems and methods, for example a mechanical coupling. The hard tube 112 can be made from any combination of sufficiently rigid materials for penetrating an obstruction 210. For example, the hard tube 112 can be constructed from metal such as 304 or 316 stainless steel or a hard polymer such as poly ether ether ketone (PEEK) that contains a 3-5 mm long stainless-steel sleeve attached to its distal end. In some embodiments, the hard tube 112 can also be constructed from multiple pieces, such as for example, a hard polymer with a short (approximately 3 mm long) stainless steel outer sleeve attached to its distal end. In some embodiments, the distal tip of hard tube 112 may also be radiused and polished, so that no sharp edges or corners are present that may puncture everting member 108 during operation of the device 100.

The dimensions of the hard tube 112 can vary in dimension depending on the application, for example, the hard tube 112 can be approximately 0.01"-0.040" in outer diameter and 0.001"-0.006" in wall thickness. Additionally, the values can be scaled based on the application. In some embodiments, the hard tube 112 can be approximately 0.022"-0.030" in outer diameter and approximately 0.0025"-0.0045" in wall thickness. The dimensions of the guidewire 106 can vary in dimension depending on the size of the hard tube 112, for example, the guidewire 106 can be approximately 0.009"-0.040" in diameter. In some embodiments, a guidewire 106 with a smaller diameter, such as approximately 0.014"-0.029", may be advanced through the hard tube 112. The guidewire 106 an be designed to freely moveable within the hard tube 112, so that it may be advanced distally down the vessel 200 or other structure whenever the hard tube 112 has been driven through an obstruction 210. In some embodiments, during initial application of the device 100, the distal end of the guidewire 106 can lie flush with, and does not extend past, the distal end of the hard tube 112. This configuration ensures that the hard tube 112 and not the soft tipped guidewire 106 drives into the obstruction 210, optimizing the ability of the device 100 to cross the obstruction 210.

In some embodiments, the hard tube 112 can be designed to extend the length of push assembly 102, plus the length of everting member 108, and can protrude past the distal tip of cannula 101, for example, a distance of 2-3 mm. When designed to extend past the distal end of cannula 101, the distal edge of hard tube 112 does not rub against the surface of everting member 108 as it is everted and re-inverted multiple times during a procedure, avoiding puncture of everting member 108 and subsequent loss of pressurization of cannula 101 (and everting member 108 and anchor 109).

In some embodiments, the hard tube 112 can include one or more coatings at its distal end, such as for example, hydrophilic coatings, anti-thrombogenic coatings, hydrophobic coatings, silicone coatings, or tetrafluoroethylene (TFE) coatings. The coatings can be on an outside surface of the hard tube 112 for assisting in passage within the cannula 101, the push assembly 102, and/or the vessel 200. Similarly, the coatings can be on an internal surface of the hard tube 112 to assist in the passage of other devices within the hard tube 112 (e.g., guidewire 106). In some embodiments, a colored marker may be present near the proximal end of the hard tube 112. For example, the marker may be aligned with the proximal end of the push assembly 102, to indicate proper positioning of the hard tube 112 within the device 100 prior to use.

Referring to FIG. 1B, a pressurized and inverted state of the device 100 is depicted. In some embodiments, upon placement of the cannula 101 at a desired location, the cannula 101 can be pressurized to anchor the device 101 in place, via injection of fluid through inflation port 110. Upon pressurization of cannula 101, anchor 109 can expand to contact and anchor against interior walls of a vessel, while everting member 108 compresses onto the hard tube 112. In some embodiments, substantially the entire length of the everting member 108 may collapse onto the hard tube 112 to securely grip the hard tube 112.

As shown in FIG. 1B, the guidewire 106 can be loaded into the pathway of the push assembly 102 and through the everting member 108 while within the push assembly 102. In some embodiments, the guidewire 106, can be dimensioned to substantially fill the interior portion of the push assembly 102 (or hard tube 112) while remaining freely moving within push assembly 102 (or hard tube 112), and can be positioned flush with the distal end of hard tube 112. For example, the interior portion of the push assembly 102 can have a diameter of 0.015"-0.030" the guidewire 106 can have a diameter of 0.014"-0.029". Having the guidewire 106 substantially fill an interior portion of the push assembly 102 or hard tube 112 can provide a preventative measure against coring when pushing the push assembly 102 or hard tube 112 into an obstruction 210 to create an opening. As would be appreciated by one skilled in the art, the guidewire 106 can be any dimension to slidably move within the push assembly 102 or hard tube 112 and also be configured to extend beyond or fall short of the distal end of the push assembly 102 and/or hard tube 112. In some embodiments, the sliding seal 104 may also be closed onto guidewire 106 to seal and hold the guidewire 106 in place (e.g., substantially flush with the distal end of the hard tube 112).

Referring to FIG. 1C a pressurized and everted state of the device 100 is depicted. In some embodiments, the everting member 108 can be everted by sliding the push assembly 102 distally relative to the cannula 101 to drive the hard tube 112 attached to the push assembly 102 in a longitudinal direction (e.g., toward an obstruction) and evert the everting member 108. As depicted in FIG. 1C, advancing the push assembly 102 into cannula 101 can cause everting member 108 to evert from the distal end of the cannula 101 and can also drive hard tube 112 forward through the everting member 108. More specifically, when the push assembly 102 is advanced in a longitudinal direction to evert the everting member 108, the everting member 108 can advance the tip of the hard tube 112 in the same direction, while providing a supporting force to enable the hard tube 112 to pierce and/or penetrate an obstruction. In some embodiments, the everting member 108 may push the hard tube 112 a distance equal to the distance of push assembly 102 advancement. It should be noted that, in some embodiments, since the everting member 108 advances in a toroidal, double walled configuration, the everting member 108 can advance the hard tube 112 a distance that is about one-half the distance of push assembly 102 advancement. In this manner, hard tube 112 may advance ahead of the leading front of the everting member 108 to penetrate the obstruction. In some embodiments, the everting member 108 may be everted and inverted sequentially to cyclically pulse the hard tube 112 into the obstruction repeatedly to create an opening into previously impenetrable obstructions 210. In some embodiments, once the hard tube 112 has been used to penetrate and/or clear an obstruction, the guidewire 106 can be advanced through the hard tube 112 and beyond the distal end of the hard tube 112.

Figure 2A:
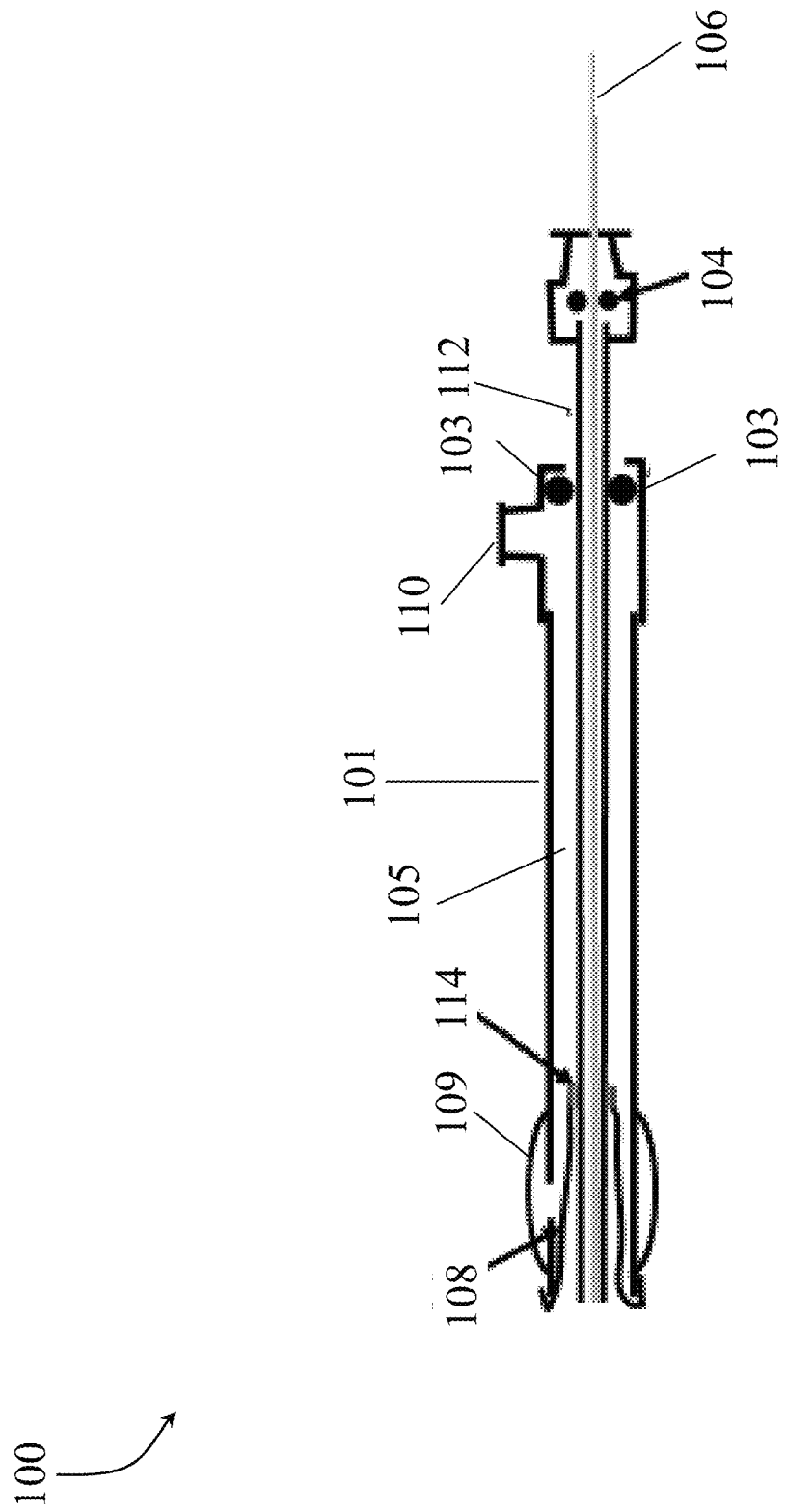
FIGS. 2A, 2B, and 2C show cross-sectional views of a device for traversing an obstruction in accordance with an embodiment of the present invention.
Figure 2B:
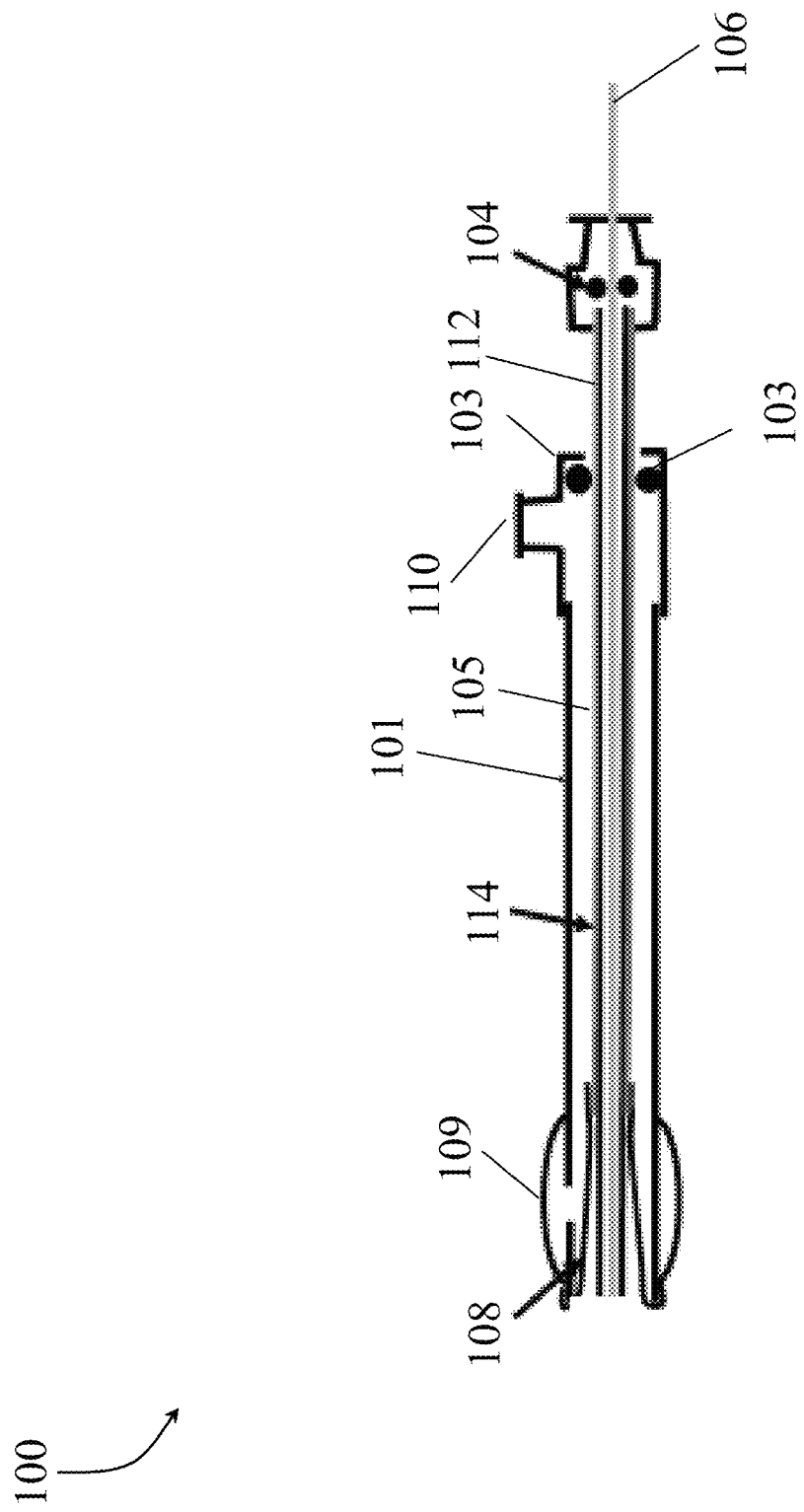
Figure 2C:
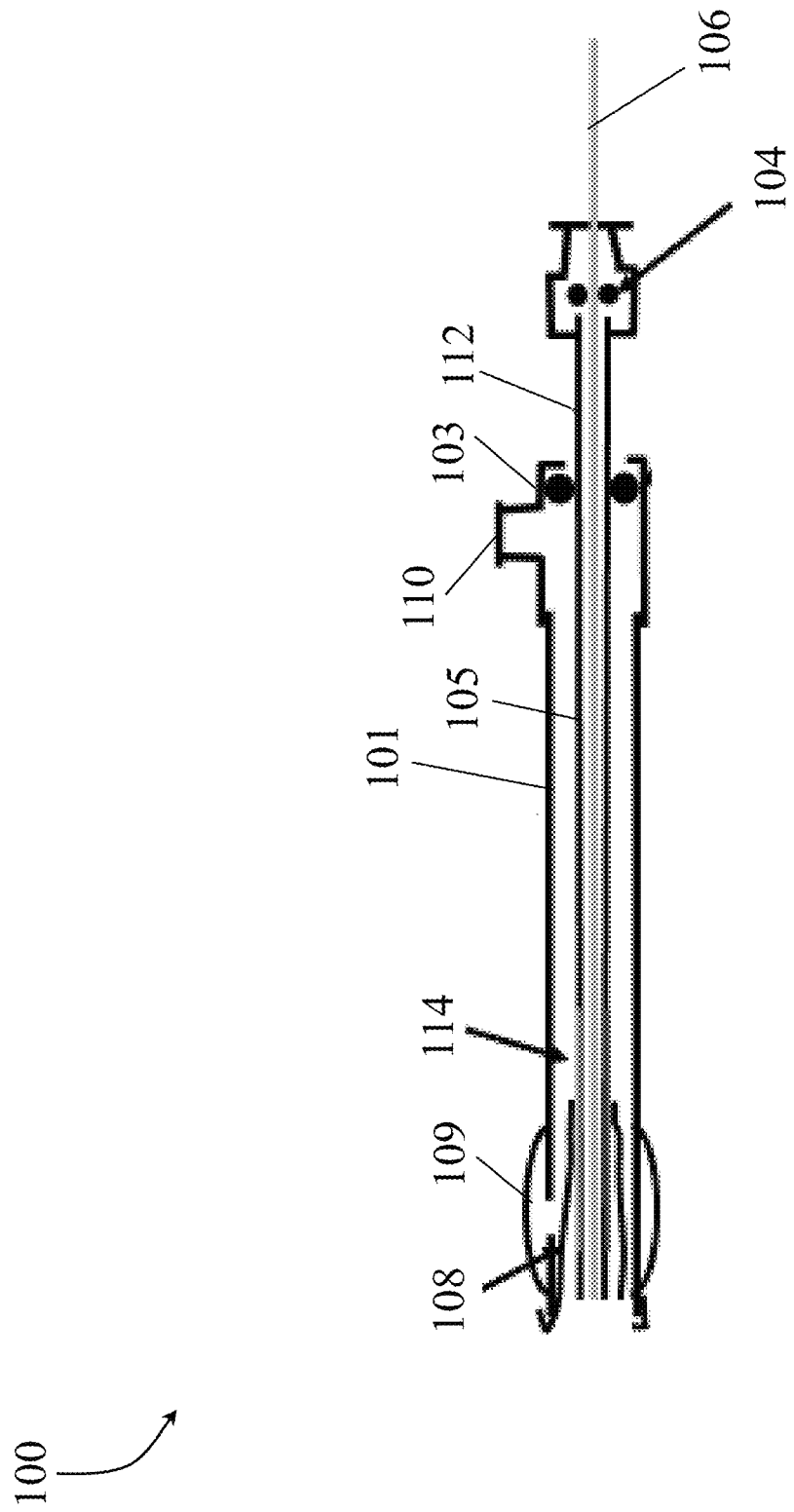

Referring to FIGS. 2A-2C, in some embodiments, the hard tube 112 can be substituted for the push assembly 102. In such an implementation, a proximal end of the hard tube 112 can extends out of the proximal end of the cannula 101, proceeding through the inflation port 110 and the lumen 105 of the cannula 101, and extend distally to or beyond the distal tip of the cannula 101. For example, the distal end of the hard tube 112 can end about 2-3 mm from the distal tip of the cannula 101. The everting member 108 can be attached to the hard tube 112 approximately 2-4 cm proximal to the distal end of the hard tube 112. In some embodiments, the proximal end of the everting member 108 may be attached to the distal end of the hard tube 112 via an adhesive bond, mechanical bond, etc. In some embodiments, the hard tube 112 can be made from a combination of materials to both provide rigidity for traversing an obstruction 210 and providing a surface for bonding with the everting member 108. For example, a stainless steel hard tube 112 may be covered with a thin polymer sleeve composed of Nylon 12 or heat shrink PET of approximately 0.0002"-0.0003" wall thickness, and the proximal end of the everting member may be heat bonded onto the polymer covered hard tube 112. The bonding surface, such as a polymer sleeve, may extend the full length of the hard tube 112, or it may cover the hard tube 112 for approximately a 4 cm length at the site of bonding to the proximal end of the everting member 108.

Referring to FIGS. 2A-2C, exemplary depictions of the device 100 with the hard tube 112 in place of the push assembly 102 are depicted. Although FIGS. 2A-2C show exemplary embodiments of the device 100 in a depressurized and inverted state, as would be appreciated by one skilled in the art, the devices 100 of FIGS. 2A-2C can operate in a same manner as the device 100 discussed with respect to FIGS. 1A-1C and as discussed in greater detail with respect to FIGS. 3A-3C. For example, the exemplary devices 100 in FIGS. 2A-2C can be pressurized and depressurized in the same manner as the device 100 discussed with respect to FIGS. 1A-1C.

Referring to FIG. 2A, in some embodiments, the proximal end of everting member 108 can be attached to hard tube 112 using an adhesive bond 114, with distal end of everting member 108 attached to the distal end of cannula 101. In some embodiments, the distal end of the hard tube 112 can extend beyond the distal end of the cannula 101 and the proximal end of the hard tube 112 can extend proximally proximal end of the cannula 101 (e.g., through the seal 103). For example, the distal end of hard tube 112 can extend approximately 1-3 mm distal to the distal end of cannula 101. In some embodiments, the sliding seal 104 can be attached to the proximal end of hard tube 112, to seal against a guidewire 106 residing within the lumen of hard tube 112, as depicted in FIG. 2A.

Referring to FIG. 2B, in some embodiments, the hard tube 112 can be covered with a thin-walled sleeve 116, that extends nearly the full length of hard tube 112. The thin-walled sleeve 116 can be constructed from a material that enables attachment of the proximal end of everting member 108 using heat bonding techniques. For example, the thin-walled sleeve 116 can be a polymer material and the everting member 108 can be composed of similar polymeric material. The material composition of both structures may be a polymer such as Nylon 12 or PET (polyethylene terephthalate). The thin-walled sleeve 116 may be a heat shrink tube that is shrunk onto hard tube 112, forming a permanent material surface for heat bonding to everting member 108. In some embodiments, several millimeters of hard tube 112 base material (e.g., stainless-steel) can remain exposed at the distal portion of hard tube 112, to ensure that maximal tip hardness is retained, for example, for insertion into obstructions.

Figure 3A:
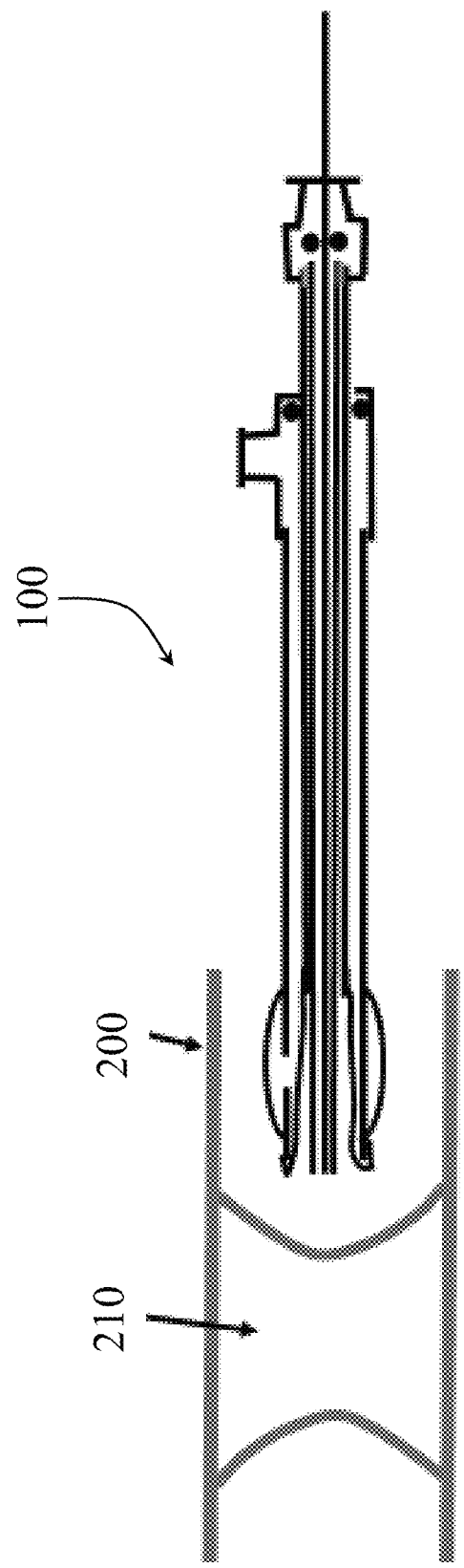
Figure 3C:
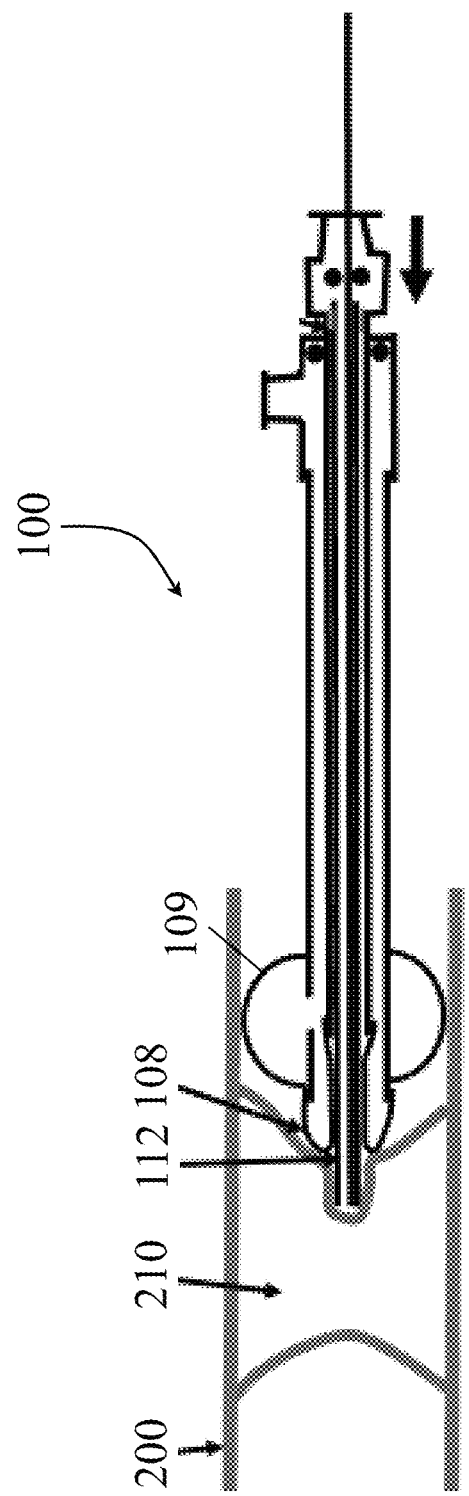

Referring to FIG. 2C, in some embodiments, a thin-walled sleeve 118 segment can be attached to a portion of hard tube 112 or push assembly 102 at the site of attachment of the proximal end of everting member 108. The length of thin-walled sleeve 118 segment, in some embodiments, can be less than half the overall length of the hard tube 112. For example, the thin-walled sleeve 118 segment can be approximately 1-5 cm in length, and it may be heat shrunk onto hard tube 112. In some embodiments, several millimeters of hard tube 112 base material (e.g., stainless-steel) can remain exposed at the distal portion of hard tube 112, to ensure that maximal tip hardness is retained, for example, for insertion into obstructions Referring to FIGS. 3A-3C, an exemplary process for using the device 100 functionality discussed with respect to FIGS. 1A-1C is depicted. Although FIGS. 3A-3C are discussed with respect to a method for using the device 100 with respect to FIGS. 1A-1C, one skilled would appreciate that a similar process can be applied to the device 100 discussed with respect to FIGS. 2A-2C. In some embodiments, the device 100 can be used to traverse and/or open a site of obstruction 210 within a vessel 200 in which the site of obstruction 210 can be completely clogged or occluded with no passage therethrough. For example, the obstruction 210 can be comprised of a relatively hard material (e.g., calcified deposits in a pipe or a "hard cap" in a blood vessel or artery). In general, the hard tube 112 may be advanced distally from the cannula 101 into the obstruction 210 by pressurization and eversion of the everting member 108.

Referring to FIG. 3A, the device 100 advanced to the site of an obstruction 210 in a vessel 200 is depicted. In FIG. 3A, the cannula 101 is in an inverted and depressurized state that can been advanced to the site of an obstruction 210 within a vessel 200. Prior to interaction with the obstruction 210, the distal end of the cannula 101 may be placed in contact with the leading edge of obstruction 210, or a few millimeters proximal to obstruction 210.

FIG. 3B depicts the cannula 101 in an inverted and pressurized state after an application of pressure to the lumen 105 of the cannula 101. The pressurization of the lumen 105 (e.g., via port 110) can cause the anchor 109 to expand and contact with the inner wall of vessel 200, to anchor the device 100 at this location. Additionally, the pressurization of the lumen 105 can cause the everting member 108 to pressurize and collapse onto and grip the push assembly 102 (or hard tube 112). The cannula 101 can be pressurized, for example, through an injection of fluid via the injection port 110. The pressurization of the cannula can cause both the anchor 109 to inflate and grip the wall of vessel 200 while the everting member 108 collapses and compresses onto the push assembly 102 (or the hard tube 112).

FIG. 3C, depicts the cannula 101 in an everted and pressurized state, after the push assembly 102 is advanced in a longitudinal direction, causing eversion of everting member 108 and advancement of the push assembly 102 (or hard tube 112) into obstruction 210. Even in situations where the obstruction 210 is dense, the push assembly 102 (or hard tube 112) can be sufficiently rigid to pierce into obstruction 210 and eventually traverse the site of obstruction 210 to clear a passageway within the vessel 200. More specifically, FIG. 3C shows that upon advancement of push assembly 102 through fluid tight seal 103 in injection port 110, the everting member 108 drives push assembly 102 (or hard tube 112) into obstruction 210. In this configuration, significant driving force can be achieved, as cannula 101 is inflated with a minimum of 6 atmospheres of pressure (approximately 90 psi), and gripping pressure is exerted on the push assembly 102 (or hard tube 112) at the point of insertion into obstruction 210.

In some embodiments, the everting member 108 is not sufficiently long to advance the push assembly 102 (or hard tube 112) through the entire obstruction 210. In such embodiments, the everting member 108 can be re-inverted without displacement of the push assembly 102 (or hard tube 112) for subsequent re-eversion and further advancement of the push assembly 102 (or hard tube 112). Thus, the device 100 can advantageously permit traversal of the entire obstruction 210 without a need to reposition and re-align the device 100 after each eversion. In some embodiments, once the obstruction 210 has been cleared by the push assembly 102 (or hard tube 112), the guidewire 106 can be advanced through the opening in the obstruction for some interventional procedures. For example, once a guidewire 106 has been placed distally through the obstruction 210, additional procedures such as stent placement, atherectomy, etc. may be performed.

In operation, the guidewire 106 can be centered inside push assembly 102 (or hard tube 112) and may be centered and anchored within the pipe, tube, vessel, artery, etc. by the pressurized anchoring member 109. Moreover, the everting member 108 may stabilize the push assembly 102 (or hard tube 112) in such centered position when the everting member 108 is pressurized as shown in FIG. 3B. Advancement of the push assembly 102 (or hard tube 112) may drive distal tip of the push assembly 102 (or hard tube 112) into the center of the obstruction 210, to reopen the obstruction.

In some embodiments, the push assembly 102 (or hard tube 112) may be cyclically advanced and retracted a short distance; e.g. 5-10 mm at a time, to serially drive a guidewire 106 with higher rigidity into the obstruction 210. In some embodiments, the cannula 101 may be depressurized and the push assembly 102 (or hard tube 112) can be pulled back, so that upon re-pressurization of cannula 101, only the everting member 108, without the push assembly 102 (or hard tube 112), is advanced through the obstruction 210. Everting member-only advancement may be performed in situations in which advancement of the push assembly 102 (or hard tube 112) preceding the everting member 108 may be dangerous; for example, if vessel curvature or the presence of a bifurcation or branch increases the potential for push assembly 102 (or hard tube 112) perforation into the sidewall.

Once an opening is initiated in the obstruction 210, if the push assembly 102 (or hard tube 112) was able to traverse the entire obstruction, the push assembly 102 (or hard tube 112) can be removed and everting member 108 can be everted into the opening created in the obstruction 210. If the push assembly 102 (or hard tube 112) is only able to partially traverse the obstruction, the device 100 can advantageously be manipulated to re-invert the everting member 108 without displacement of the push assembly 102 (or hard tube 112) from within the partially formed opening.

In some embodiments, the everting member 108 can then be depressurized again and the push assembly 102 (or hard tube 112) can be slid back into substantial longitudinal alignment with the distal end of the distal end 101b of the cannula 101. In some embodiments, while the everting member 108 is depressurized, the cannula 101 can be advanced such that the distal end 101b of the cannula is aligned with the tip of the push assembly 102 (or hard tube 112). The push assembly 102 (or hard tube 112) can then be further advanced into the obstruction by repeating the steps described above until the obstruction has been traversed by the push assembly 102 (or hard tube 112).

Although described in portions hereof as providing access across a site of obstruction within a vessel within a body, the invention can provide access across other sites of obstruction as well. For example, the invention can be used to provide access across an obstruction in a cavity or other type of opening. Furthermore, the invention is not limited to use within the medical field. The sleeve can, for instance, be delivered across an obstruction in a pipeline, drain, tube, or other type of passage, etc. Additionally, since the balloon may be designed to seek the path of least resistance, as described above, the invention may be used to seek out hidden or unknown pathways through various sites of obstruction. In other embodiments, the invention may be equipped with an object or device to be delivered across a site of obstruction. In such an embodiment, an object may be situated on the distal end 101b ref cannula 101, a distal end of everting member 108, or on a distal end of the hard tube 112 so that as the everting member 108 extends through the site of obstruction, the object is delivered to an area distal to the site of obstruction.

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about", "generally", and "approximately" are intended to cover variations that may existing in the upper and lower limits of the ranges of subjective or objective values, such as variations in properties, parameters, sizes, and dimensions. In one non-limiting example, the terms "about", "generally", and "approximately" mean at, or plus 10 percent or less, or minus 10 percent or less. In one non-limiting example, the terms "about", "generally", and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A device for providing access across a site of obstruction comprising:
    a cannula having a proximal end, a distal end, and a lumen extending therebetween;
    a hard tube being slidably movable longitudinally within the lumen, the hard tube being longer than the cannula; and
    an everting member having a first end coupled to the distal end of the cannula, and a second end fixed to a distal end of the hard tube when the everting member is in a pressurized state and a depressurized state, such that upon pressurization, the everting member pulls the hard tube distally during eversion,
    wherein the hard tube is disposed distal to the everting member when the everting member is in an everted position outside the cannula.

2. The device of claim 1, further comprising an anchoring member circumferentially placed about an outer surface of the cannula and in fluid communication with the lumen.

3. The device of claim 2, wherein the lumen provides a path along which pressurizing fluid can be introduced and evacuated from the cannula, such that in the presence of pressurizing fluid, the anchoring member inflates while the everting member compresses onto the hard tube, and in the absence of pressurizing fluid, the anchoring member deflates while the everting member decompresses from the hard tube.

4. The device of claim 2, wherein the anchoring member being in the fluid communication with the lumen of the cannula and being expandable from a depressurized position to a pressurized position anchors the cannula near a site of obstruction when the lumen is pressurized to an anchoring pressure sufficient to anchor the cannula in proximity to the site of obstruction.

5. The device of claim 1, further comprising a bushing disposed at the distal end of the cannula to couple the first end of the everting member to the distal end of the cannula.

6. The device of claim 1, further comprising a sealing member disposed between walls of the lumen and the hard tube to seal the lumen.

7. The device of claim 1, further comprising a sealing member disposed between walls of a pathway of the hard tube and &guidewire to seal the pathway.

8. The device of claim 1, wherein the hard tube is configured to receive a guidewire therethrough.

9. The device of claim 1, wherein the hard tube is covered, along its entire length, with a polymer sleeve or heat shrink PET sleeve.

10. The device of claim 1, wherein the everting member pulls the hard tube distally during eversion as a function of the pressurization.

11. A system for providing access across a site of obstruction comprising:
a cannula having a proximal end, a distal end, and a lumen extending therebetween;
an everting member, having a first end coupled to the distal end of the cannula and a second end;
a push assembly, positioned within the lumen, having a pathway along its entire length, the push assembly being slidably disposed across the proximal end of the cannula into the lumen of the cannula and being connected at its distal end to the second end of the everting member, such that advancement of the push assembly along the lumen of the cannula moves the everting member from an inverted position within the lumen of the cannula to an everted position outside the cannula; and
a hard tube fixedly attached to the push assembly, when the everting member is in a pressurized and depressurized state, such that the hard tube is slidably movable with the push assembly, within the lumen, the hard tube being disposed distal to the everting member when the everting member is in the everted position outside the cannula.

12. The system of claim 11, further comprising an anchoring member circumferentially placed about an outer surface of the cannula and in fluid communication with the lumen.

13. The system of claim 12, wherein the lumen provides a path along which pressurizing fluid can be introduced and evacuated from the cannula, such that in the presence of pressurizing fluid, the anchoring member inflates while the everting member compresses onto the hard tube, and in the absence of pressurizing fluid, the anchoring member deflates while the everting member decompresses from the hard tube.

14. The system of claim 12, wherein the anchoring member being in the fluid communication with the lumen of the cannula and being expandable from a depressurized position to a pressurized position anchors the cannula near a site of obstruction when the lumen is pressurized to an anchoring pressure sufficient to anchor the cannula in proximity to the site of obstruction.

15. The system of claim 11, further comprising a guidewire configured for passage through at least one of the push assembly and the hard tube.

16. The system of claim 11, further comprising an injection port configured to couple to a pressurization source configured to inject fluid to pressurize the lumen and extract the fluid to depressurize the lumen.

* * * * *